US006264680B1

United States Patent
Ash (10) Patent No.: US 6,264,680 B1
(45) Date of Patent: Jul. 24, 2001

(54) APPARATUSES AND PROCESSES FOR WHOLE-BODY HYPERTHERMIA

(75) Inventor: Stephen R. Ash, Lafayette, IN (US)

(73) Assignee: ViaCirQ, Inc., Pittsburgh, PA (US)

( * ) Notice: Subject to any disclaimer, the term of this patent is extended or adjusted under 35 U.S.C. 154(b) by 0 days.

(21) Appl. No.: 09/235,449

(22) Filed: Jan. 22, 1999

Related U.S. Application Data (60) Provisional application No. 60/072,238, filed on Jan. 23, 1998.

(51) Int. Cl.$^7$ .................................................. A61F 7/00
(52) U.S. Cl. .............................................. 607/106; 604/6.13
(58) Field of Search ................................. 604/4–6, 507, 604/27, 28, 113, 114, 6.13; 210/321.6, 321.71

(56) References Cited

U.S. PATENT DOCUMENTS

| 3,608,729 | 9/1971 | Haselden . | |
|---|---|---|---|
| 4,479,798 | 10/1984 | Parks . | |
| 4,950,225 | 8/1990 | Davidner et al. . | |
| 5,085,781 | * 2/1992 | Tsuru et al. | 210/692 |
| 5,277,820 | 1/1994 | Ash | 210/646 |
| 5,354,277 | 10/1994 | Guzman et al. . | |
| 5,476,444 | 12/1995 | Keeling et al. | 604/4 |
| 5,536,412 | 7/1996 | Ash . | |
| 5,674,190 | * 10/1997 | Kelly | 604/4 |
| 5,855,782 | * 1/1999 | Falkenhagen et al. | 210/323.1 |

FOREIGN PATENT DOCUMENTS

| 4024355 | 8/1990 | (DE) . |
|---|---|---|
| 9506145 B1 | 8/1992 | (KR) . |

OTHER PUBLICATIONS

V. Beral, T.A. Peterman, R.L. Berkelman, H.W. Jaffe, "Kaposi's Sarcoma Among Persons With AIDS: A Sexually Transmitted Infection?", *The Lancet*, vol. 335, pp. 123–128 (Jan. 20, 1990).

J.M. Bull, D. Lees, W. Schuette, J. Whang–Peng, R. Smith, G. Bynum, E.R. Atkinson, J.S. Gottdiener, H.R. Gralnick, T.H. Shawker, V.T. DeVita, Jr., "Whole Body Hyperthermia: A Phase–I Trial Of A Potential Adjuvant To Chemotherapy", *Ann. Internal Medicine*, vol. 90, pp. 317–323 (1979).

R. Cavaliere, E.C. Ciogatto, B.C. Giovanella, C. Heidelberger, R.O. Johnson, M. Margottini, B. Mondovi, G. Moricca, A. Rossi–Fanelli, "Selected Heat Sensitivity Of Cancer Cells: Biochemical And Clinical Studies", *Cancer*, vol. 20, pp. 1351–1381 (Sep. 1967).

(List continued on next page.)

*Primary Examiner*—Linda C. M. Dvorak
*Assistant Examiner*—David M. Ruddy
(74) *Attorney, Agent, or Firm*—Webb Ziesenheim Logsdon Orkin & Hanson, P.C.

(57) ABSTRACT

Apparatuses for use in whole body hypothermia include a high-flow hyperthermia circuit coupled to a low-flow dialysis circuit in a manner which reduces tensioning of membranes in the dialyzer of the dialysis circuit. The arrangement thereby allows proper membrane movement to assist in mixing a sorbent suspension circulated on the sorbent side of the dialyzer. Additional dialysis apparatuses include advantageous disposable packs including the dialyzer, sorbent heat exchangers arranged to cooperate with heating elements on base units of the apparatuses, and adaptations for very high flow rates useful in the hyperthermic treatment of cancers.

8 Claims, 5 Drawing Sheets

OTHER PUBLICATIONS

N.B. Hornback, "Historical Aspects Of Hyperthermia In Cancer Therapy", *Radiologic Clinic of North America*, vol. 27, No. 3, pp. 481–488 (May 1989).

J.M. Larkin, W.S. Edwards, D.E. Smith, P.J. Clark, "Systemic Thermotherapy: Description Of A Method And Physiologic Tolerance In Clinical Subjects", *Cancer*, vol. 40, pp. 3155–3159 (Dec. 1977).

J.S. McDougal, L.S. Martin, S.P. Cort, M. Mozen, C.M. Heldebrant, B.L. Evatt, "Thermal Inactivation Of The Acquired Immunodeficiency Syndrome Virus, Human T Lymphotropic Virus–III/Lymphadenopathy–Associated Virus, With Special Reference To Antihemophilic Factor", *J. Clin. Invest.*, vol. 76, pp. 875–877 (Aug. 1985).

B. Mondovi, R. Strom, G. Rotilio, A.F. Agro, R. Cavaliere, A.R. Fanelli, "The Biochemical Mechanism Of Selective Heat Sensitivity Of Cancer Cells. I. Studies On Cellular Respiration", *Europ. J. Cancer*, vol. 5, pp. 129–136 (1969).

L.C. Parks, D. Minaberry, D.P. Smith, W.A. Neely, "Treatment Of Far–Advanced Bronchogenic Carcinoma By Extracorporeally Induced Systemic Hyperthermia", *J. Thorac. Cardiovasc. Surg.*, vol. 78, pp. 883–892 (1979).

H.I. Robins, A. Hugander, J.D. Cohen, "Whole Body Hyperthermia In The Treatment Of Neoplastic Disease", *Radiologic Clinics of North America*, vol. 27, No. 3, pp. 603–610 (May 1989).

R.–N. Shen, N.B. Hornback, H. Shidnia, L. Lu, H.E. Broxmeyer, Z. Brahmi, "Effect Of Whole–Body Hyperthermia And Cyclophosphamide On Natural Killer Cell Activity In Murine Erythroleukemia", *Cancer Research*, vol. 48, pp. 4561–4563 (Aug. 15, 1988).

B. Spire, D. Dormont, F. Barré–Sinoussi, L. Montagnier, J.C. Chermann, "Inactivation Of Lymphadenopathy–Associated Virus By Heat, Gamma Rays, And Ultraviolet Light", *The Lancet*, pp. 188–189 (Jan. 26, 1985).

M.B. Yatvin, "An Approach To AIDS Therapy Using Hyperthermia And Membrane Modification", *Medical Hypotheses*, vol. 27, pp. 163–165 (1988).

M.B. Yatvin, W.A. Cramp, "Role Of Cellular Membranes In Hyperthermia: Some Observations And Theories Reviewed", *Int. J. Hyperthermia*, vol. 9, No. 2, pp. 165–185 (1993).

M.B. Yatvin, M.H.B. Stowell, C.R. Steinhart, "Shedding Light On The Use Of Heat To Treat HIV Infections", *Oncology*, vol. 50, pp. 380–389 (1993).

\* cited by examiner

APPARATUSES AND PROCESSES FOR WHOLE-BODY HYPERTHERMIA

CROSS REFERENCE TO RELATED APPLICATION

This application claims priority from U.S. Provisional patent application Ser. No. 60/072,238 filed Jan. 23, 1998.

FIELD OF THE INVENTION

The present invention relates to a specialized device for whole-body hyperthermia, including extracorporeal blood heating and dialysis.

BACKGROUND OF THE INVENTION

Whole body hyperthermia (WBHT) as a treatment for neoplasms has been carefully studied and applied since the 1960's (3,4,27). Prior to that period there were multiple reports of tumor regression coincident with induced fever. Biochemical studies of the effects of hyperthermia have indicated that temperatures greater than 41° C. induce necrosis of some types of tumor (3,5). In the body, there are additional physiologic effects by which hyperthermia induces tumor necrosis. In both normal and tumorous tissue, hyperthermia causes an initial vasodilation of blood vessels with a resulting increase in blood flow. Then, there is a decrease in blood flow due to autoregulation and vasoconstriction (6). Tumor tissues have less vascular reactivity to autoregulate blood flow, and are therefore more prone than normal tissues to the effects of high temperature during either local hyperthermia or WBHT (7).

It is now generally accepted that hyperthermia is a useful therapy in treatment of cancers, and regional hyperthermia for accessible tumors is used in every major cancer therapy center in the U.S. Regional hyperthermia is a valuable adjunct to radiation and chemotherapy, because it carries low risk, has few side effects, and often exerts its best effects in patients whose lesions are unresponsive to radiation or chemotherapy (3). In metastatic solid tissue tumors, WBHT is used more than regional hyperthermia, since it is difficult to apply regional therapy to lesions in the abdomen or chest. Even in patients who have failed radiation or chemotherapy, there is a partial remission of the tumors in about half of the patients, and complete remission in a few patients. These results are similar to those obtained with many drugs; however, with drug therapy of cancer, the incidence of side-effects is approximately 100%. Though there are some side-effects of WBHT, most of them are short-lived and not serious.

Kaposi's sarcoma (KS) is the most common neoplasm of patients with AIDS, being seen primarily in the male homosexual AIDS population (8). Unlike the classical KS, the AIDS-related form is often aggressive, presenting with multiple, large cutaneous tumors and early visceral dissemination. The etiology of KS in these patients is uncertain. Cytomegalic viral infections, other sexually transmitted organisms, volatile nitrate inhalation, oncogenes, hormones and HLA type have all been suggested as possible co-factors. KS is currently reported as the primary diagnosis in 13% of hospital admissions of all AIDS patients (9) and the disfiguring disease accounts for substantial morbidity.

Of all tumors, KS seems to be the most sensitive to systemic hyperthermia. In a 1985 survey of 21 patients treated with hyperthermia for cancer, the only patient with complete remission was one with KS (10). According to the investigators, this patient is the only one of the 21 treated who is still alive; the KS lesions have not recurred. A case report in 1990 indicated dramatic resolution of KS lesions during and shortly after a single WBHT treatment (11). These lesions had not recurred one year later (12) nor three years later. Numerous patients with HIV and Kaposi's sarcoma have been treated by WBHT. Most of the patients had remission of Kaposi's lesions and diminished evidence of HIV for 4 months (120 days) after treatment (29).

Hyperthermia also helps to resolve many bacterial infections. The fever response in mammals evolved specifically for this reason, and beneficial effects of fever in survival of animals after gram negative blood infection has been reported (13). Hyperthermia also has a beneficial effect in resolution of many viral infections. Hornback and co-workers have studied infection of mice by Friend virus complex, a retrovirus complex similar to HIV which causes a uniformly fatal erythroleukemia in mice, with devastating effects on T-cells and natural killer cells similar to those of HIV. This disease can be partially controlled by WBHT at 40° C. (once weekly for 2 weeks). Mice receiving WBHT after injection with Friend virus lived twice as long as untreated controls, and longer than those treated with cyclosporin alone (14,15). Natural killer cell function is also increased by the WBHT therapy versus controls (14,15).

The HIV virus is somewhat heat sensitive. McDougal, et al. incubated HIV at temperatures ranging from 37° to 60° and found the log kill followed first order kinetics (16). In the natural liquid state, HIV was 40% inactivated after 30 minutes at 42° C., and 100% inactivated at 56° C. (17). Importantly, HIV-infected lymphocytes are very effectively killed by 42° C. temperature. Since only a small portion of lymphocytes are HIV infected, this means that the surviving cells will be free to perform their usual immunologic functions, unimpeded by HIV. Even if some HIV-infected lymphocytes do survive, they have a change in surface antigens to allow recognition by the immune system.

The beneficial effects of a single WBHT in treatment of HIV and Kaposi's sarcoma are no longer a theoretical possibility but a demonstrated reality. One study indicates that of 31 patients with HIV and Kaposi's sarcoma treated with WBHT, 70% had complete or partial regression of Kaposi's sarcoma lesions and these patients had an increase of CD4 counts for an average of 120 days. Adenopathy and oral leukoplakia resolved in all patients. The treatment was most effective when the pre-treatment CD4 count was over $50/mm^3$. In no patient was HIV activity stimulated by WBHT, as determined by many antigen markers (29).

An article by Milton B. Yatvin, PhD, indicates that "the initial effect of hyperthermia on cells is mediated via the heat-induced disorganization of membrane lipids" (28). This effect was further defined in later studies (18,19). Yatvin also described a variety of simple compounds which have fluidizing effects on lipid bilayer membranes similar to heat, and exert antiviral effects on HIV and other viral infections (including ethanol, anesthetics, AL721, adamantane, and a common food additive called butylated hydroxytoluene or BHT) (18). In later work, Yatvin suggested that the effects of heat on virally-loaded cells was enhanced by fluidizing chemical agents (27,18). These articles demonstrate that WBHT should have positive effects on HIV infection, and that these effects can be improved by addition of some simple chemicals during or before WBHT.

There are many methods for inducing WBHT including paraffin wax baths, radiant heat chambers, microwave heat chambers, water blankets, and extracorporeal blood heating. These methods have been used mostly in treatment of patients with far-advanced metastatic cancer. Even in these frail patients, core temperature can be maintained at 42° C. for one to two hours without untoward effects on cardiovascular, renal, or liver function, though there usually is elevation of serum transaminases, creatinine phosphokinase, and lactate dehydrogenase (4). Three instances of mild neurologic damage were noted in Parks' patients in association with hypophosphatemia during treatment, but no significant problems occurred once phosphate levels were maintained (20). Larkin also reported two deaths in patients receiving WBHT at 41.5 to 42° C. for 1½ to 2 hours; however, these patients had massive tumors in the liver, and by-products of tumor necrosis contributed to the death of these patients (21). In review of prior studies Yatvin, Stowell and Steinhart found only 6 deaths in 275 hyperthermic treatments of debilitated patients with carcinoma, representing a mortality of only 2% (27).

Extracorporeal WBH is usually accomplished using a relatively simplistic circuit containing only a blood pump and a heat exchanger to heat the blood (22). The blood flow rate through the extracorporeal system has been high, at 2–3 liters per minute. During this procedure, and other WBH techniques, the patient is warmed to a core temperature of 41.50 to 42° C. for two hours or more. Sedation is required and often general anesthesia and intubation is performed (22). In the mildly sedated patient, the brain stem responds with hyperventilation, to increase heat loss. Blood alkalosis results, leading to decreases in potassium, calcium, phosphate, and magnesium (as these substances transfer into cells or bone) (23). In a generally anesthetized patient on mechanical ventilation, normal ventilation can be provided. However, the increased body metabolic rate and centralization of blood flow leads to acidosis, with increases in potassium, calcium, phosphate and magnesium (24). Frequent blood chemistries must be measured during the treatment, so that these changes in blood chemistries can be corrected by intravenous infusion of various electrolytes. Following WBH, there is often a persisting deficiency in potassium, calcium, and phosphate unless these have been aggressively replaced during the treatment. Often, there is moderate damage to liver, muscles, and kidneys during the treatment, demonstrated by changes in enzyme and toxin levels in the blood (23,25,26).

Clinically recognizable complications of hyperthermia depend to some degree upon the method of administration, whether by direct skin contact, radiant heat, or heating of the blood, and on the core temperature obtained and length of exposure. Skin burns with hyperthermia generally occur only when created by skin contact or radiant heat. Studies in cancer patients have shown a significant incidence of fatigue, peripheral neuropathy, vomiting, diarrhea, and arrhythmias. However, these occurred mostly in severely debilitated patients with Karnofsky Scores less than 50% (1,2).

In treatment of patients with HIV and Kaposi's sarcoma, hyperthermia also is relatively safe. In a study of 31 patients with HIV and Kaposi's sarcoma treated by extracorporeal WBHT with a relatively low blood flow rate of 300–400 ml/min (29), there was no significant morbidity associated with the treatment, though two patients had intravascular coagulopathy (without signs of bleeding) and several patients had pressure point skin damage. There were two patient deaths within 120 days of the procedure, one from intracerebral bleed due to a pre-existing intracerebral Berry aneurysm (a rare condition) and one from pulmonary edema and cardiac arrhythmia following overly aggressive fluid therapy (in a patient who had pre-existing pulmonary disease). The overall mortality of this study was only 7%; the mortality rate would have been zero if patients with abnormal pulmonary status had been excluded from the study, and if the patient with the very rare cerebral vascular condition had not been treated.

Among the known protocols for extracorporeal heating of blood, various difficulties persist, including elevated serum transaminases and bilirubin, instances of neurologic damage associated with serum hypophosphatemia, risk due to abnormal pH or to abnormal sodium, sodium bicarbonate or potassium levels, and possible death from massive tumor necrosis. Previously attempted treatments of human immunodeficiency virus with hyperthermia have included only relatively minor measures to maintain normal blood physiology (the sodium bicarbonate addition of Davidner et al., for example). A need therefore remains for a more reliable, simpler and more comprehensive extracorporeal hyperthermia treatment, and an apparatus for performing such treatment, in which unwanted side effects are reduced or eliminated altogether. The present invention addresses this need.

SUMMARY OF THE INVENTION

One preferred embodiment of the invention provides a method for performing whole body hyperthermia on a patient. The method includes circulating blood of the patient through a high-flow hyperthermia circuit at a rate of at least 1500 ml/min, the hyperthermia circuit including a blood access line for drawing blood from a patient, a pump, a heat exchanger for heating the blood to a temperature of at least 40° C., and a blood return line for returning the blood to the patient after heating in the heat exchanger. The method also includes diverting a portion of the blood circulating in the high-flow hyperthermia circuit to a low-flow dialysis circuit, and circulating the blood in the low-flow dialysis circuit at a rate of 200 to 800 ml/min. The low-flow dialysis circuit includes:

- a blood inflow line having a first end connected to the hyperthermia circuit, for diverting blood into the dialysis circuit from the hyperthermia circuit;
- a dialyzer having a blood side and a sorbent side separated by dialysis membranes, the membranes being compliantly formed;
- means for applying alternating negative pressure and positive pressure on the sorbent side of the dialyzer;
- a blood inlet to the blood side of the dialyzer, a second end of the blood inflow line being connected to the blood inlet;
- a blood outlet from the blood side of the dialyzer;
- a blood outflow line having a first end connected to the blood outlet, and a second end connected to the hyperthermia circuit;
- a sorbent circuit for circulating a sorbent suspension through the sorbent side of the dialyzer. Further, during operation of the high-flow hyperthermia circuit and the low-flow dialysis circuit, the dialyzer membranes expand and compress in response to the alternating negative pressure and positive pressure on the sorbent side of the dialyzer, so as to circulate and agitate a sorbent suspension in the sorbent side whereby effective mixing of the sorbent suspension is maintained. In more preferred forms, the method also includes heating the sorbent suspension in a heat exchanger, so as to decrease the transfer of heat from the blood to the sorbent suspension. In addition, the blood inflow line is preferably connected to the high-flow hyperthermia circuit at a location downstream of the blood outflow line, for example advantageously occurring on opposed sides of the pump of the hyperthermia circuit.

In another embodiment, the invention provides an apparatus for use in whole body hyperthermia treatment of a patient. The apparatus includes a high-flow hyperthermia circuit equipped to circulate blood therethrough at a rate of at least 1500 ml/min, the high-flow hyperthermia circuit including a blood access line for drawing blood from a patient, a pump, a heat exchanger for heating the blood to a temperature of at least 40° C., and a blood return line for returning the blood to the patient after heating in the heat exchanger. Also included is a low-flow dialysis circuit equipped to circulate blood therethrough at a rate of 200 to 800 ml/min, the low-flow dialysis circuit coupled to the hyperthermia circuit and effective to divert from the hyperthermia circuit a portion of the blood circulating therein. The low-flow dialysis circuit, in turn, includes:

a blood inflow line having a first end connected to the hyperthermia circuit, for diverting blood into the dialysis circuit from the hyperthermia circuit;

a dialyzer having a blood side and a sorbent side separated by dialysis membranes, the membranes being compliantly formed;

means for applying alternating negative pressure and positive pressure on the sorbent side of the dialyzer;

a blood inlet to the blood side of the dialyzer, a second end of the blood inflow line being connected to the blood inlet;

a blood outlet from the blood side of the dialyzer;

a blood outflow line having a first end connected to the blood outlet, and a second end connected to the hyperthermia circuit;

a sorbent circuit for circulating a sorbent suspension through the sorbent side of the dialyzer.

Further, the apparatus of the invention is configured such that during operation of the high-flow hyperthermia circuit and the low-flow dialysis circuit, the dialyzer membranes expand and compress in response to the alternating negative pressure and positive pressure on the sorbent side of the dialyzer, so as to circulate and agitate a sorbent suspension in the sorbent side whereby effective mixing of the sorbent suspension is maintained.

Another embodiment of the invention provides a disposable pack for use with a dialysis instrument. The disposable pack includes a pack mount member, and a plate dialyzer mounted on the pack mount member having a blood side with a blood inlet and a blood outlet, and a sorbent side with a sorbent inlet and a sorbent outlet. A blood inflow tube communicates with the blood inlet of the plate dialyzer, for passing blood from a patient into the blood side of the dialyzer. A blood outflow tube communicates with the blood outlet of the plate dialyzer, for passing blood out of the blood side of the dialyzer. Sorbent circulation tubes communicate with the sorbent side of the dialyzer via the sorbent inlet and sorbent outlet, for circulating sorbent through the sorbent side of the dialyzer. A flow-through heat exchanger communicates with the sorbent circulation tubes, for heating sorbent flowing through the heat exchanger. The disposable pack also preferably includes an accumulator reservoir mounted on the pack mount member and communicating with the sorbent circulation tubes, the accumulator reservoir being operable to alternately accumulate and expel sorbent in response to positive pressure and negative pressure alternately applied to the accumulator reservoir.

In another embodiment, the invention provides a process for preparing a sorbent suspension, which includes combining an aqueous solution having dissolved calcium ions with an aqueous solution having dissolved phosphate ions, wherein the combining is in the presence of a powdered surface adsorptive agent so as to form precipitated calcium phosphate both on the adsorptive agent and freely in the suspension. This process is advantageously carried out by:

(a) combining water, activated charcoal powder and a flow-inducing agent;

(b) adding separate solutions containing, respectively, dissolved calcium chloride and dissolved disodium phosphate, to the product of step (a);

(c) agitating the product of step (b);

(d) adding a sodium, calcium, magnesium and potassium-loaded cation exchange resin to the product of step (c);

(e) agitating the product of step (d);

(f) adding sodium bicarbonate powder to the product of step (e); and (g) agitating the product of step (f).

Still another preferred embodiment of the invention provides a dialysis system which has a base unit equipped with a source of positive pressure and negative pressure, a heating element, and receiving means for receiving a heat exchanger in heat exchange relationship with the heating element. The system also includes a disposable pack for use with the base unit, including a pack mount member, a plate dialyzer mounted to the pack mount member, the dialyzer having a blood side with a blood inlet and a blood outlet, and a sorbent side with a sorbent inlet and a sorbent outlet, a blood inflow tube communicating with the blood inlet of the plate dialyzer, for passing blood from a patient into the blood side of the dialyzer, a blood outflow tube communicating with the blood outlet of the plate dialyzer, for passing blood out of the blood side of the dialyzer, sorbent circulation tubes communicating with the sorbent side of the dialyzer via the sorbent inlet and sorbent outlet, for circulating sorbent through the sorbent side of the dialyzer, an accumulator reservoir mounted to the pack mount member, the accumulator reservoir communicating with the sorbent circulation tubes, the accumulator reservoir being operable to alternately accumulate and expel sorbent suspension in response to positive pressure and negative pressure alternately applied to the accumulator reservoir, the accumulator reservoir being connected to the source of positive pressure and negative pressure of the base unit, and a flow-through heat exchanger communicating with the sorbent circulation tubes, for heating sorbent flowing through the heat exchanger, the heat exchanger cooperating with the receiving means of the base unit to removably position the heat exchanger in heat exchange relationship with the heating element of the base unit.

It is an object of the invention to provide an apparatus which can effectively be used in whole body hyperthermia to control patient blood chemistries during the treatments.

Other objects of the invention are to provide a sorbent suspension composition which is highly effective for use in sorbent-based hemodialysis to control patient blood calcium and phosphate levels in addition to other blood chemistries, and to provide processes for effectively preparing such compositions.

Another object of the invention is to provide apparatuses for use in supplying hemodialysis during whole body hyperthermia, which apparatuses includes compliant membranes which promote mixing of sorbent suspensions and which are not overly tensioned by high rates of blood flow used in hyperthermia circuits during the treatments.

Additional objects of the invention relate to the provision of dialysis systems including convenient disposable packs and advantageous arrangements for circulating and heating sorbent suspensions utilized in the systems.

Additional embodiments, features and advantages of the present invention will be apparent from the following description.

DESCRIPTION OF THE PREFERRED EMBODIMENTS

For the purpose of promoting an understanding of the principles of the invention, reference will now be made to certain embodiments thereof and specific language will be used to describe the same. It will be understood, however, that no limitation of the scope of the invention is thereby intended, such alterations, further modifications and applications of the principles of the invention being contemplated as would normally occur to one skilled in the art to which the invention pertains.

The present invention enables the application of sorbent-based hemodialysis to hyperthermia treatments in a highly effective fashion. This hemodialysis technology involves the use of a specialized sorbent suspension as the hemodialysing solution. The dialysis procedure during hyperthermia allows many important electrolytes to be regulated and kept at appropriate levels in the blood. In addition, many toxins, for example those incident to death of virally infected cells and/or Kaposi's sarcoma cells, are removed.

Figure 1:
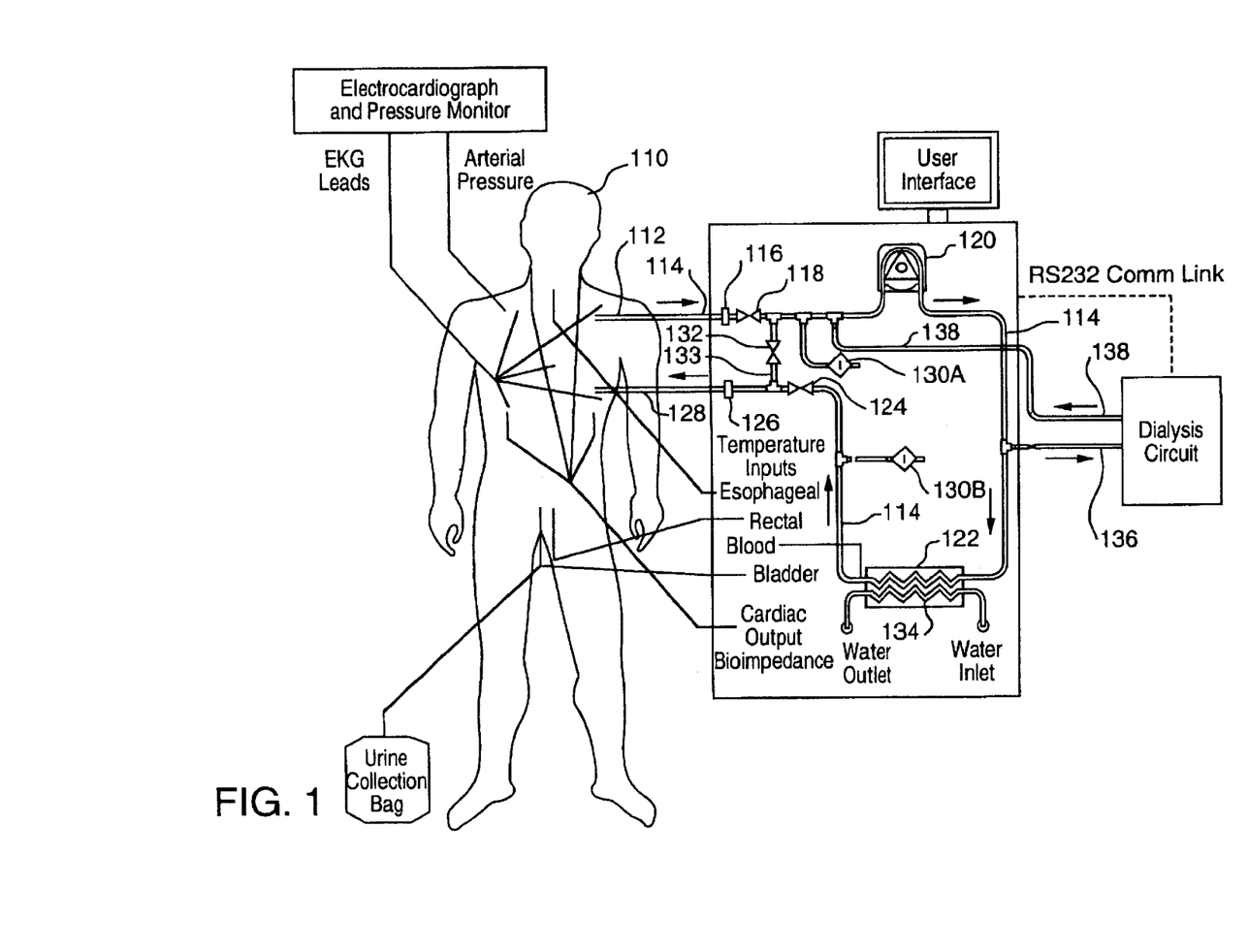
FIG. 1 is a schematic diagram illustrating a preferred apparatus for conducting whole body hyperthermia.

FIG. 1 illustrates a preferred apparatus for achieving whole body hyperthermia according to the present invention. The patient 110 is positioned for treatment, and optionally covered with a solar blanket or similar heat-retaining (and optionally heat-producing) device. A blood outflow catheter 112 connects the patient to extracorporeal blood hyperthermia circuit line 114. The line 114 passes through blood inflow bubble detector 116 and blood inflow occluder 118. Line 114 then transports blood to a pump 120 (roller pump), and then on to and through a blood side of heat exchanger 122. After exiting heat exchanger 122, line 114 passes through blood outflow occluder 124 and blood outflow bubble detector 126. A blood return catheter 128 returns the blood to the patient 110. Pressure sensors 130A and 130B are connected to line 114 to measure the pressure of the blood flow in line 114 exiting and re-entering patient 110, respectively. Rinse line 133 is seated in rinse occluder 132, which can be opened to facilitate the conduct of rinse operations. Heat Exchanger 122 includes a heat-transfer fluid side 134 through which heat transfer fluid, for example water, is passed to heat the blood passing through the blood side of heat exchanger 122.

Dialysis circuit inflow line 136 connects the blood side of a dialysis circuit to the hyperthermia circuit line 114 at a location following pump 120 in the hyperthermia circuit, and dialysis circuit outflow line 138 connects the blood side of the dialysis circuit to the hyperthermia circuit line 114 at a point after pump 120 in the hyperthermia circuit. Thus, blood is drawn into the dialysis circuit from the hyperthermia circuit via line 136, and is returned to the hyperthermia circuit via line 138. In this fashion, a relatively higher flow rate (for example about 1000–4000 ml/min) can be maintained in the hyperthermia circuit and a relatively lower flow rate can be maintained in the dialysis circuit (typically about 200–600 ml/min), while avoiding tensioning of the dialysis membranes employed, as discussed further below.

Figure 2:
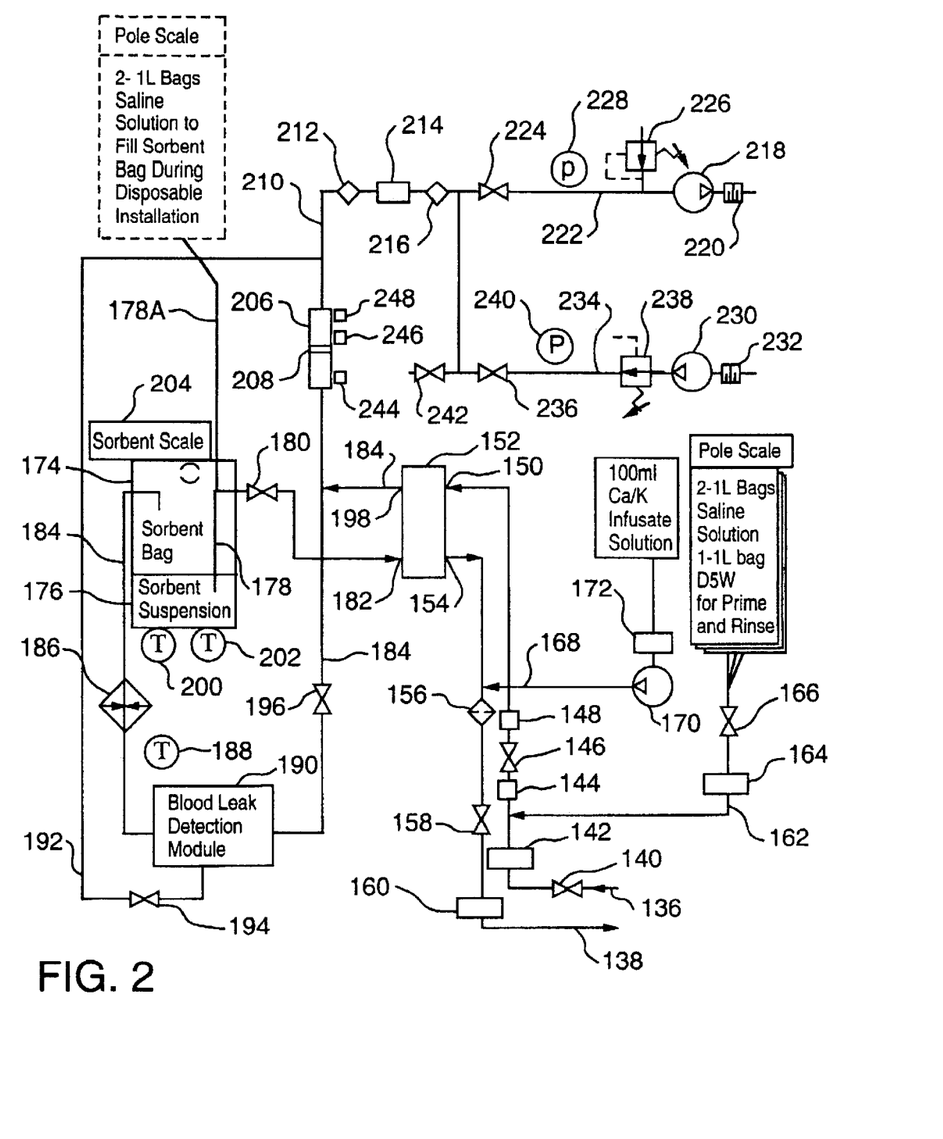
FIG. 2 is a schematic diagram of the hydraulics of a preferred hemodialysis instrument used in the conduct of whole body hyperthermia.

With reference now to FIG. 2, the preferred dialysis circuit will be discussed in greater detail. Blood passes from the hyperthermia blood circuit (FIG. 1) into the dialysis circuit via inflow line 136. Line 136 passes through blood inflow occluder 140, bubble detector 142, blood flow rate start sensor 144, blood flow occluder 146, and blood flow rate stop sensor 148. Line 136 then leads into blood inlet 150 of the blood side of plate dialyzer 152. Plate dialyzer 152 has blood outlet 154 to which blood outlet line 138 is attached. Blood outlet line 138 then passes through blood filter/bubble trap 156, blood outflow occluder 158, and bubble detector 160, after which it is connected to tubing 114 of hyperthermia circuit (FIG. 1).

Prime/rinse line 162 is connected to tubing 136 at a location intermediate bubble detector 142 and blood flow rate sensor 144, for input of priming and rinsing solutions (e.g. from bags of solution hung on a pole scale, as illustrated) during priming and rinsing operations of the system. Line 162 includes prime/rinse bubble detector 164 and prime/rinse occluder 166.

Infusate line 168 is connected to tubing 138 at a location intermediate dialyzer blood outlet 154 and blood filter/bubble trap 156, for infusion of solutions (e.g. 100 ml Ca/K infusate solution) to the patient. An infusion pump 170 and a drip chamber/drop counter combination 172 are also provided for these purposes.

On the sorbent side of the dialysis system of FIG. 2, provided is a sorbent bag 174 including a sorbent suspension 176. Sorbent inflow line 178 has an opening residing in the sorbent suspension 176 for withdrawing suspension 176 from the bag 174. Sorbent inflow line 178 is seated in sorbent inflow occluder 180, and then passes to sorbent inlet 182 of the sorbent side of dialyzer 152.

Sorbent inflow line 178 is also connected to sorbent fill line 178A, providing a line for fluid connection to bags of saline (e.g. hanging on a pole scale) or the like, to fill the sorbent bag with saline prior to commencing treatment. Fill line 178A can then be disconnected.

Sorbent return line 184 has an opening residing in sorbent bag 174, for return of sorbent suspension 176 to sorbent bag 174. Positioned in sorbent return line 184 is sorbent heat exchanger 186, for heating the sorbent suspension to prevent the sorbent system from acting as a heat sink which draws substantial heat from the blood in the hypothermia circuit. Sorbent heater 186 has associated therewith temperature sensor 188 for monitoring the temperature of the sorbent.

Also positioned in sorbent return line 184 is blood leak detection module 190, which draws a filtrate from the sorbent suspension and assays the filtrate for the presence of blood (hemoglobin). Module 190 is connected via line 192 to a vacuum/pressure source which enables the module to obtain the filtrate. Positioned within line 192 is filtrate occluder 194, which is automatically opened and closed periodically to draw the filtrate for processing in the blood leak detection module 190.

Sorbent return line 184 is also seated in sorbent out occluder 196, which is also opened and closed at controlled intervals to facilitate the sorbent circulation cycle through dialyzer 152. Sorbent return line 184 is connected to dialyzer 152 at sorbent outlet 198 of the sorbent side of dialyzer 152.

Temperature sensors 200 and 202 are connected to sorbent bag 174, and serve to monitor the temperature of the sorbent suspension 176 within the sorbent bag 174. In addition, sorbant bag 174 is hung on sorbent scale 204, which is used to monitor the weight of the sorbent suspension.

Circulation of sorbent suspension 176 in the sorbent system of blood on the blood side of dialyzer 152 is powered via the action of accumulator reservoir 206. Accumulator reservoir 206 has an internal diaphragm 208 which reciprocates upwardly and downwardly within reservoir 206 in response to alternating negative pressure (vacuum) and positive pressure applied to reservoir 206 via vacuum/pressure line 210. Vacuum/pressure line 210 includes disposable biohazard filter 212 and disposable coupling 214, such that these disposable elements may be removed and disposed of after treatments. Vacuum/pressure line 210 also includes an internal biohazard filter 216.

Vacuum/pressure line 210 is connected to vacuum pump 218 with associated muffler 220 via vacuum line 222. Vacuum line 222 includes inflow air valve 224, which is automatically opened and closed at controlled intervals to participate in the provision of alternating vacuum and pressure to accumulator reservoir 206. Also associated with vacuum pump 218 and vacuum line 222 are a vacuum regulator 226 and vacuum transducer 228, as illustrated.

Vacuum/pressure line 210 is connected to pressure pump 230 with associated muffler 232 via pressure line 234. Pressure line 234 has located therein outflow air valve 236, which is automatically opened and closed at controlled intervals. Flow of the suspension is generally countercurrent with respect to blood flow, and is in one aspect both bidirectional between the accumulator 206 and dialyzer 152, and circular between the dialyzer 152 and sorbent bag 174.

To accomplish this, during the first part of blood inflow, occluder 180 on the sorbent inflow line 178 automatically opens, and occluder 196 automatically closes, and vacuum is applied via accumulator reservoir 206, allowing sorbent suspension 176 to flow from the sorbent bag 174 through the dialyzer 152, filling the accumulator reservoir 206. Occluder 180 then closes and remains closed during the remainder of blood inflow and all of outflow, when pressure applied by the accumulator reservoir 206 returns some suspension to the dialyzer 152 and passes some through sorbent return line 184 (with occluder 196 now automatically opened) to return to the sorbent bag 174. This, along with the expansion and contraction of the dialyzer membranes, keeps the sorbent suspension well mixed at the dialyzer membrane surface.

In the preferred system, the priming fluid for the blood side of the dialysis system is 5% dextrose in water (D5W). This solution flows into blood inflow line 136 via line 162, powered by the expansion and contraction of the membranes of plate dialyzer 152 in response to the alternating positive and negative pressure applied via accumulator reservoir 206. During priming or rinse operations, priming/rinse occluder 166 automatically opens and blood inflow occluder 140 automatically closes, and occluders 146 and 158 alternately open and close to cause unidirectional flow of fluid through dialyzer 152 powered by the expansion and contraction of the dialysis membranes of dialyzer 152 in response to the alternating negative and positive pressure applied to the sorbent side by accumulator reservoir 206. Priming or rinsing fluid is thus pulled into the system rather than blood, and circulated through dialyzer 152. Priming operations may be automated, and serve to remove air from lines and the dialyzer 152 on both the blood and dialysate sides. Rinse operations may also be automated, and programmed to occur both periodically during treatment (e.g. to periodically return fluids (e.g. saline)) to the patient, and/or upon completion of the treatment.

During blood inflow cycles, prime/rinse occluder 166 automatically closes and blood inflow occluder 140 automatically opens. Blood is thus pulled into the system from the hyperthermia circuit, via blood inflow line 136 and circulated from the hyperthermia circuit through dialyzer 152 through the action of the dialysis membranes and alternate opening and closing of occluders 146 and 158, in similar fashion to the prime/rinse fluids described above.

In the dialysis circuit, blood flow rates of about 200–800 ml/minute will be typical, with flow rates in the range of about 200–600 ml/minute being preferred.

In the hyperthermia circiut, blood flow rates of up to about 4000 ml/min are preferred, typically in the range of about 1500 ml/min to about 2000 ml/min. These high flow rates can be achieved by alteration of the headgear of the roller pump 120 (FIG. 1) to provide for higher revolutions per minute. Such extremely high flow rates are important for use of the apparatus in the treatment of certain cancer patients, for example patients having metastatic solid tissue tumors such as metastatic non-small cell lung cancer tumors, and allow for quick heating of patients. This enables the optimization of treatment time prior to upregulation of heat shock proteins in the patients.

Other features in the device and its use also assist in achieving these high flow rates while avoiding excessive pressure in blood inflow and outflow lines. For these purposes, blood access is "veno-venous", with the blood inflow catheter 112 (FIG. 1) positioned in the superior vena cava via the internal jugular and the blood outflow catheter 128 positioned in the femoral vein. The venous catheters utilized are preferably thin-walled, wire supported catheters, ranging in size from 10–18 French, placed percutaneously. As well, in the preferred, high-flow device, the blood return circuit from heat exchanger 134 to blood return catheter 128 can optionally be devoid of blood filters such as bubble filter 126 which cause substantial pressure drop at the preferred blood flow rates employed. Heat exchanger 134 can also be equipped with a conical-shaped top (a feature of commercially-available heat exchangers such as the Electromedics D1079E heat exchanger), to gather any bubbles present serve as the final bubble trap before returning to the patient. The conical-shaped top, in turn, can be equipped with a Luer connection or similar device for sterile removal of any trapped air (e.g. by syringe).

For whole body hyperthermic treatment of metastatic solid tissue tumors such as metastatic non-small cell lung cancer tumors (e.g. metastasis to the contralateral lung), about a two-hour treatment at a patient core temperature of 42.5° C. is performed. For such treatments, the water temperature in the heat exchanger 134 is preferably set to a maximum of about 52° C., several degrees higher than that typically used for therapies for HIV infection.

Figure 3:
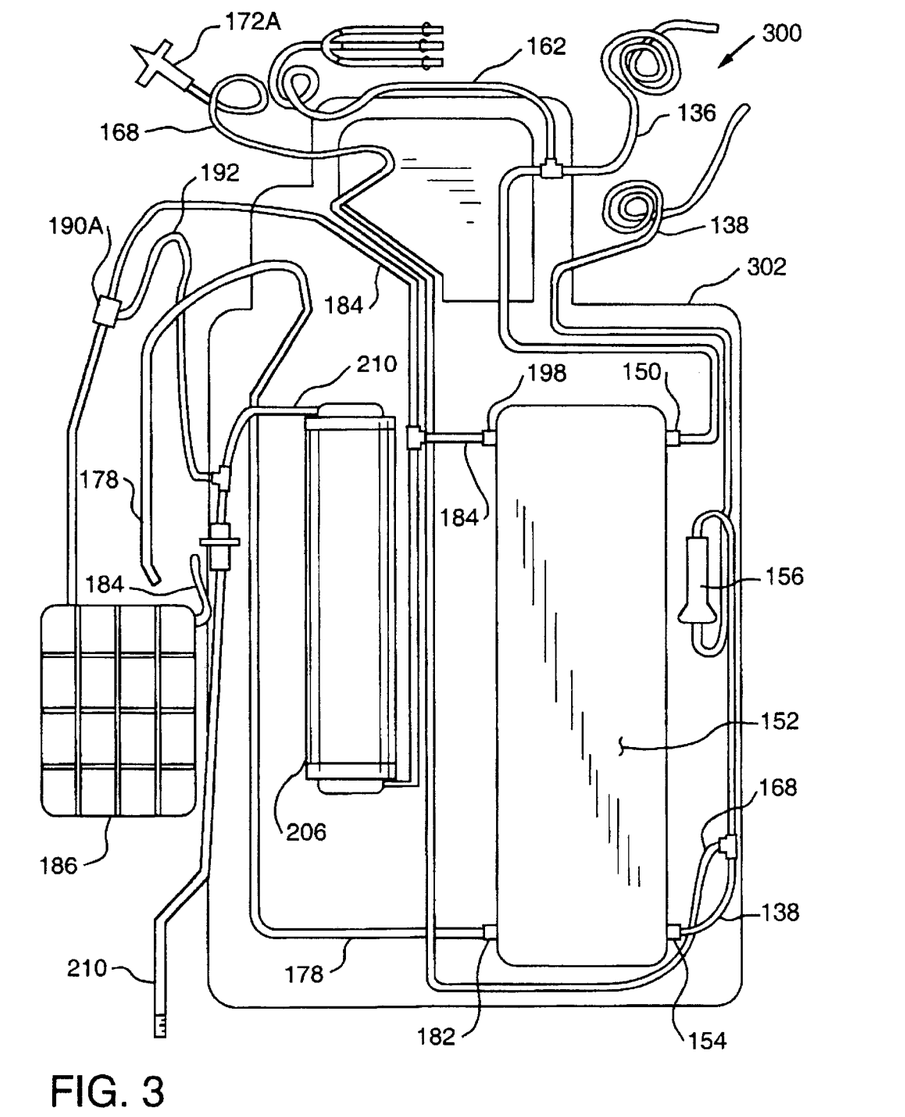
FIG. 3 illustrates a disposable pack including disposable elements of a hemodialysis instrument of the invention.

Referring now to FIGS. 3–6, illustrated are a disposable pack and a base unit which can be used together to provide the features of the dialysis circuit shown in FIG. 2. In particular, shown in FIG. 3 is disposable pack 300, containing various elements of the dialysis system which may be disposed of after treatment. Pack 300 includes pack mount member 302, to which various components of the pack 300 are attached. Pack mount member 302, in a preferred form includes structures such as depressions, openings, and the like, to hold the various mounted elements in convenient locations. Pack 300 generally includes dialyzer 152, blood inflow and outflow lines 136 and 138 connected to blood inlet 150 and blood outlet 154 of dialyzer 152, respectively, blood filter/bubble trap 156, sorbent inflow and return lines 178 and 184 connected to sorbent inlet 182 and sorbent outlet 198 of dialyzer 152, respectively, and heat exchanger 186 for heating the sorbent suspension 176. Filtrate generator 190A (a component of blood leak detection module 190) is located in sorbent return line 184, and is connected to filtrate tube 192 which in turn connects to vacuum/pressure line 210 to provide means for forming the filtrate sample for assay. Pack 300 also includes sterile solution input line 162 (for prime/rinse operations), and infusate line 168 with drip chamber 172A. Pack 300 further includes accumulator reservoir 206 connected to and powered via vacuum/pressure line 210.

Figure 4:
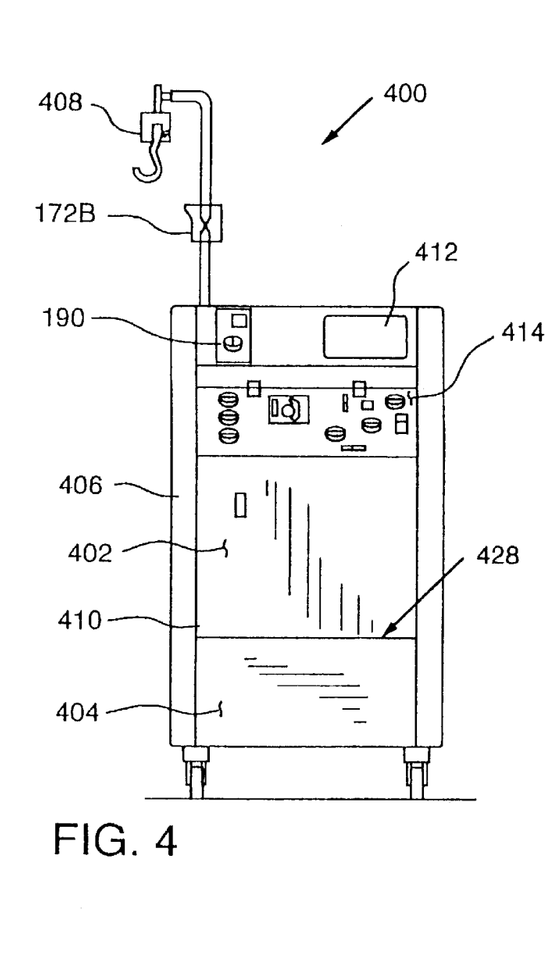
FIG. 4 provides a front, perspective view of a dialysis base unit of a preferred hemodialysis system, which can be used in conjunction with the disposable pack illustrated in FIG. 3.
Figure 5:
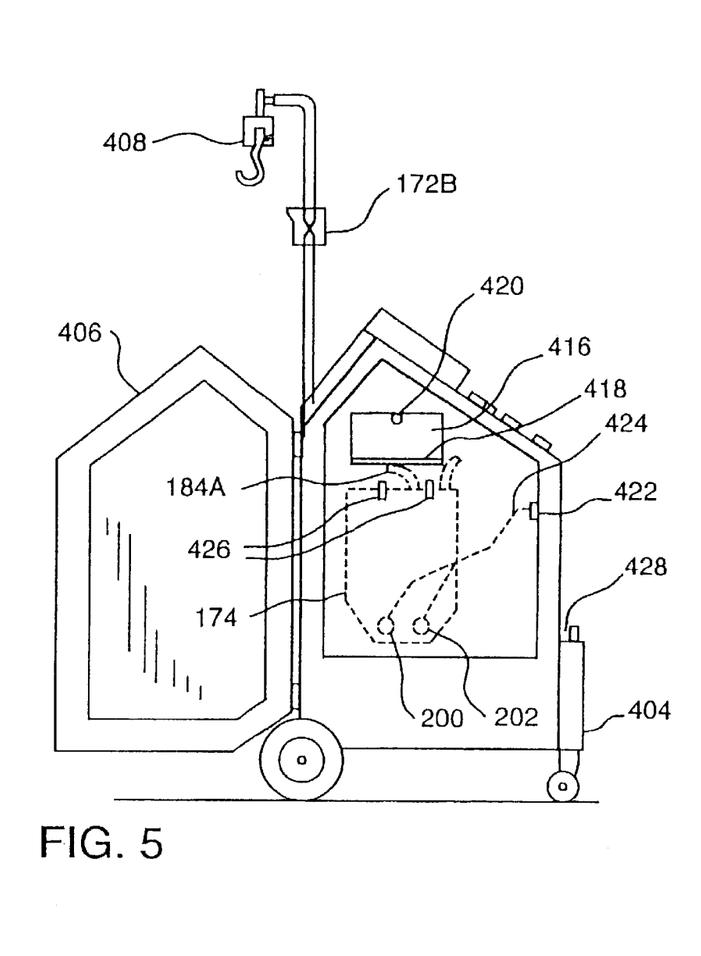
FIG. 5 provides a left-end view of the base unit illustrated in FIG. 4, with a door opened to show components within.
Figure 6:
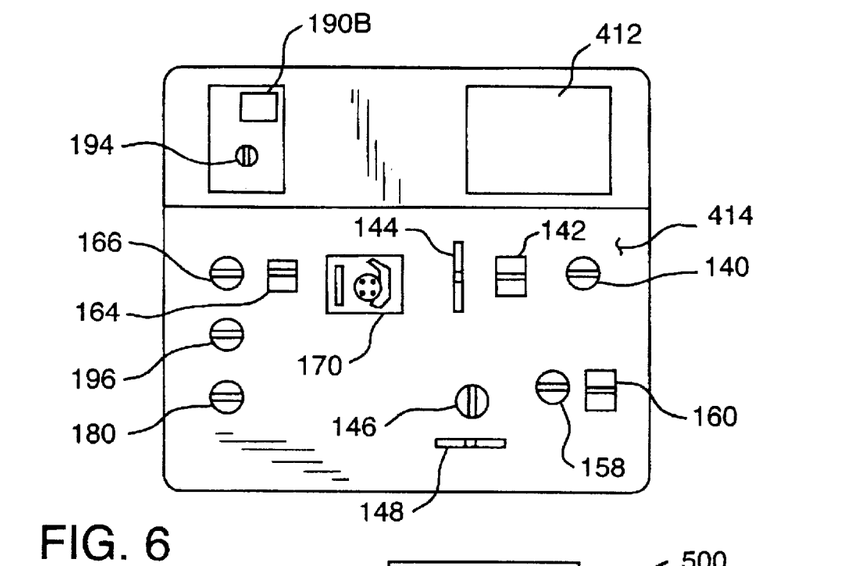
FIG. 6 provides an enlarged view of the upper surface of the base unit shown in FIG. 4, to more clearly illustrate components mounted thereon.

Shown in FIGS. 4–6 are various components of a dialysis base unit 400 for use with disposable pack 300. With reference to FIG. 4, shown is an overall perspective view of base unit 400. Base unit 400 includes a service door 402, a pneumatics drawer 404 (containing vacuum/pressure components as described above), a sorbent chamber door 406, components of blood leak detection module 190 (discussed below), a drop counter 172B for infusate line 168, a removable I.V. pole with pole scale 408, and a vacuum/pressure port 410 leading to the vacuum/pressure feed system described in FIG. 2. Base unit 400 also includes a control panel 412 and an upper surface generally denoted at 414 which contains a number of components of the system, as described further below in conjunction with FIG. 6.

Referring now also to FIG. 5, shown is a left-side view of the base unit 400 illustrated in FIG. 4, with hinged sorbent chamber door 406 open to reveal components within. In particular, shown are a heating plate 416 having a surface correspondingly configured to a surface of heat exchanger 186 (e.g. both generally flat), to optimize heat exchange therebetween. Heating plate 416 includes slot 418 near the bottom thereof to receive the bottom edge of heat exchanger 186. Also provided is a latch 420 which can be rotated to secure or release the heat exchanger 186 to or from the heating plate 416, and plug 422 for receiving the leads 424 (phantom) from temperature sensors 200 and 202 on sorbent bag 174. In addition, provided are hooks 424 for hanging sorbent bag 174 (shown in phantom).

FIG. 5 also illustrates that pneumatics drawer 404 protrudes outwardly in relation to service door 402, creating a ledge upon which is provided slot 428 for receiving the bottom edge of disposable pack 300 when mounted on the front of base unit 400. Also, shown in phantom are sorbent removal tube 178A and sorbent return tube 184A which form a part of sorbent line 178 and sorbent line 184 of the dialysis system, respectively (see FIG. 2).

Referring now to FIG. 6, shown is an enlarged view of upper surface 414 of base unit 400. Mounted on surface 414 are blood inflow occluders 140 and 146, bubble detectors 142 and 160, blood outflow occluder 158, and blood flow rate sensors 144 and 148. Also mounted on surface 414 are prime/rinse bubble detector 164, prime/rinse occluder 166, sorbent inflow occluder 180, and sorbent outflow occluder 196. In addition, surface 414 also has mounted thereon hemoglobin indicator cassette 190B which together with filtrate generator 190A provides blood leak detection module 190 (see FIG. 2). Filtrate occluder 194 is also mounted on surface 414.

For setup of the dialysis system shown in FIGS. 3–6, saline bags can be hung on pole scale 408 of base unit 400. Sorbent bag 174 can then be hung on hooks 426, and the bottom edge of the disposable pack, assembled as shown in FIG. 3, can be placed into groove 428 on the front of base unit 400. The upper part of pack 300, which is configured with openings to avoid covering up components, rests generally on the front half of upper surface 414. Heat exchanger 186 can be mounted and secured to heating plate 416, and vacuum/pressure tube 210 connected to vacuum/pressure port 410. Sorbent fill tubing 178A can be connected to sorbent outflow line 178, and used to drain the saline bags into the sorbent bag 174 (and the bag agitated), after which the sorbent outflow line 178 occuring on sorbent bag 174 can be connected to a corresponding segment of sorbent outflow line 178 connected to the sorbent inlet 182 of dialyzer 152. Blood inflow line 136 can be seated in blood inflow occluder 140, bubble detector 142, blood flow rate start sensor 144, blood inflow occluder 146, and blood flow rate stop sensor 148. Blood outflow line 138 can be seated in blood outflow occluder 158 and bubble detector 160. Sorbent inflow line can be seated in sorbent inflow occluder 180, and sorbent outflow line can be seated in sorbent outflow occluder 196. Prime/rinse line 162 can be seated in prime/rinse bubble detector 164 and prime/rinse occluder 166. Filtrate generator 190A can then be installed into the hemoglobin indicator cassette 190B of blood leak detection module 190, and line 192 seated into filtrate occluder 194. Infusate line 168 can be installed into infusate pump 170.

An infusate bag connected to infusate line 168 via drip chamber 172A can be filled with a calcium/potassium infusate solution. The bag can be spiked and the drip chamber 172A primed. Drip chamber 172A is installed in drop counter 172B. Prime and rinse solutions can be connected to prime/rinse line 162. During a prime cycle, the rinse solutions can be manually clamped off to enable feed of only the prime solution to the system. Thereafter, the manual clamps can be removed to allow flow of rinse solutions into the system during rinse cycles.

Figure 7:
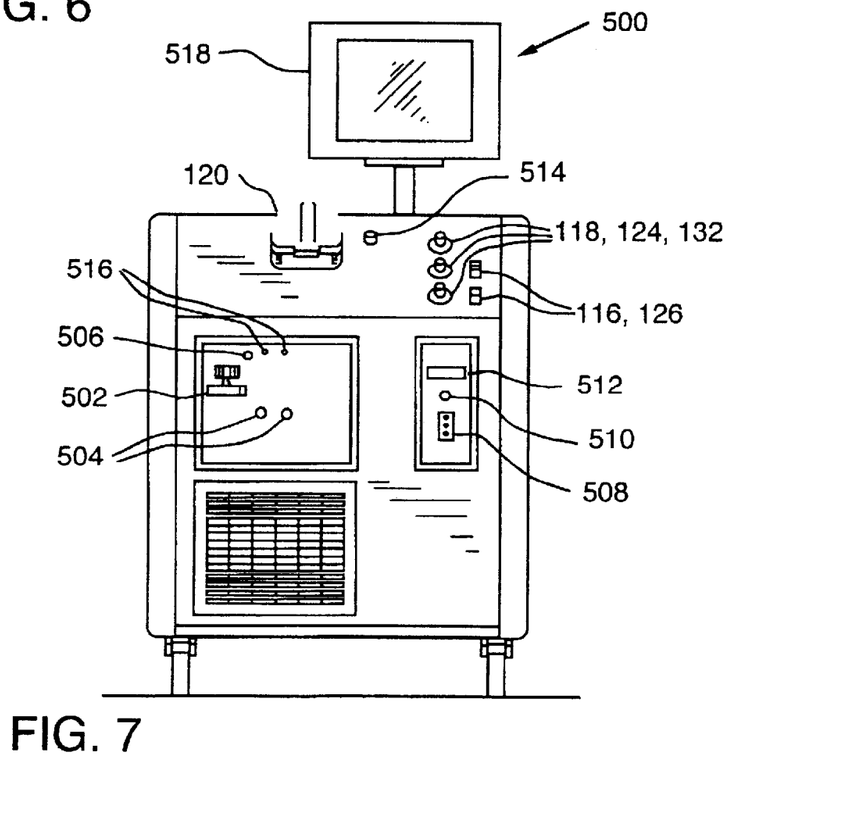
FIG. 7 provides a perspective view of a hyperthermia base unit of a preferred system, which can be used in providing a high-flow hyperthermia circuit.

With reference now to FIGS. 1 and 7, shown in FIG. 7 is a hyperthermia base unit 500 which can be used in the provision of the high-flow hyperthermia circuit shown in FIG. 1. Hyperthermia base unit 500 generally includes a wheeled cart having mounted thereon components of the high-flow circuit or which cooperate with such circuit. Included on base unit 500 are pump 120, blood inflow and outflow and rinse occluders 118, 124 and 132, and bubble detectors 116 and 126. Also included are a bracket 502 for holding heat exchanger 122, water line connectors 504 for the water inlet and water outlet of heat exchanger 122, and a blood temperature monitor 506 for measuring the temperature of blood in the circuit. The hyperthermia base 500 also includes input plugs 508 for the various patient temperature monitors employed, and input plug 510 for the cardiac output bioimpedance monitor employed. A floppy disk drive 510 is also located on the front of unit 500, to provide the ability to store data relative to treatments on the disk. A blood pump speed control knob 514 allows users to control the speed of pump 120. Pressure monitor transducer ports 516 are provided to cooperate with monitors 130A and 130B. In addition, a user interface 518, for example a computer touch-screen, is provided on base unit 500 to allow users to interface with a system computer.

As will be appreciated, dialysis base unit 400 and hyperthermia base unit 500 can be together be used to conveniently provide a whole body hyperthermia system as illustrated in FIGS. 1 and 2, by connecting blood inflow and outflow tubes 136 and 138 of the dialysis circuit (located on dialysis base 400) to appropriate connectors of the high-flow hyperthermia circuit (located on hyperthermia base unit 500). In addition, a communication link can be established between computers on the two base units using a standard cable.

As shown in FIG. 1, for whole body hyperthermia, the blood side of the dialysis apparatus is coupled to a hyperthermia circuit in which relatively high blood flow rates are maintained with a roller pump. Such high blood flow rates can cause increased tensioning of the dialyzer membranes on the blood side if the dialysis circuit is not properly connected to the hyperthermia circuit. Such increased tensioning results in restricted movement of the membranes, thus reducing sorbent mixing otherwise provided by the expansion and compression of the compliant membranes. The coupling of the dialysis circuit as shown in FIG. 2, with a blood inflow line 136 connected generally downstream of the blood outflow line 138 and preferably located on opposed sides of roller pump 120 in the system, deleterious increased membrane tensioning is minimized or avoided. Prevention of localized concentrations or dilutions of components in the sorbent suspension is thus achieved, improving the efficacy of treatment.

The membranes used for sorbent-based dialysis preferably allow passage of soluble chemicals under about 5,000 molecular weight. The first function of hemodialysis with sorbent suspensions is to correct abnormalities in cationic blood electrolytes including sodium, potassium, calcium, magnesium and hydrogen ions (blood pH). This is achieved by loading the cation exchanger in the sorbent with sufficient cation amounts to be at equilibrium with the desired (normal) blood levels. If the blood concentration of a particular cation is lower than the equilibrium level, the cation will be released from the cation exchanger. If the blood concentration is above normal, the cation will be absorbed by the cation exchanger.

There are many dialyzer membranes which are known for use in dialysing body fluids such as blood, and these membranes may be used with the sorbent suspension as though the sorbent suspension were a simple dialysis solution. One suitable membrane of this type is a cellulosic membrane composed of regenerated cuproammonium cellulose (Cuprophan).

In a preferred dialysis circuit, the dialyzer can be a 1.6m$^2$ COBE parallel screen-plate dialyzer having dialysis membranes composed of regenerated cuproammonium cellulose (Cuprophan) and having a functional molecular weight cut-off of about 3000 daltons, i.e. only molecules of about 3000 daltons or less will pass through the membrane.

The sorbent suspension used in the invention works generally as follows. When blood opposes the sorbent suspension, separated only by the dialysis membrane, diffusion causes many chemicals to pass from the blood into the sorbent suspension on the other side of the membrane. Depending upon the binding characteristics of the sorbents, some chemicals remain at low concentration in the sorbent suspensions (and are therefore efficiently removed from the blood) and others reach concentrations similar to the blood (and are therefore not removed from the blood). Inclusion of certain chemicals in the sorbent suspension composition can partially saturate sorbent binding sites, and cause return of those chemicals to the blood during treatment. Thus, the sorbent suspension may be tailored to remove very specific compounds from the blood, without removing others.

The sorbent suspensions used in the invention generally include powdered surface adsorptive agents, physiologic electrolytes and macromolecular flow inducing agents. In general, these components are present in effective amounts to achieve the desired removal of substances from the electrolyte balance in the blood of the patient while maintaining the stability and fluidity of the sorbent suspension. The powdered surface adsorptive agent is usually activated charcoal, preferably with an average particle diameter not exceeding about 100 microns. Even more preferably, the average particle diameter does not exceed 50 microns. Macromolecular flow inducing agents such as glycol derivatives help to maintain the flow properties and stability of the particle suspensions.

The electrolytes in the sorbent suspension typically include one or more selected from sodium, chloride, bicarbonate, potassium, calcium, magnesium, or any other electrolytes to be regulated in the patient.

The sorbent suspensions also may include ion-exchange substances to bind ions, such as ammonia, which may appear in the patient's blood. Many suitable ion exchangers including polymeric ion exchangers, e.g. polystyrene sulfonate, and zeolites, are known in the art and can be used in the present invention. When included, the ion-exchanger is preferably a cation-exchange resin, which is desirably loaded with one or more cations representing electrolytes occurring in blood. For example, to date, sodium polystyrene sulfonate has been a preferred cation exchange resin. For use in conjunction with whole body hyperthermia, the cation exchangers are preferably heavily loaded with Ca, K and Mg ions at the start of hyperthermia in an amount to be substantially in equilibrium with the normal blood concentration of these cations.

The surface adsorptive agent, electrolytes, flow inducing agents and any other additives will usually comprise about 5% to 30% by weight of the sorbent suspension formulation as a whole, with the remainder being water. Typically, solid sorbents will comprise about 2% to 25% by weight of the suspension formulation, and electrolytes will comprise about 1% to 5% by weight of the suspension formulation. Within these parameters, more preferred sorbent suspension formulations comprise about 2% to 20% by weight powdered surface adsorptive agent, up to about 10% by weight ion-exchanger, and up to about 1% by weight flow or surface active agent such as a polyol and/or polyvinylpyrrolidone (PVP).

In accordance with one aspect of the invention, the sorbent suspension also includes solid or precipitated calcium phosphate, which is used to assist in the control of calcium and phosphate levels in the blood of the patient. Controlling plasma phosphate concentration is somewhat more complicated than controlling other blood components. In the body, calcium and phosphate concentration are determined by their mathematical product. When the concentration of calcium in blood plasma increases, calcium phosphate precipitates on bone and the plasma phosphate level falls. Conversely, when plasma calcium concentration decreases, calcium phosphate is solubilized and plasma phosphate levels increase. In the present invention, the calcium phosphate precipitate in the sorbent suspension effectively mimics the body's calcium phosphate system, achieving control of calcium and phosphate levels. Thus, when the blood phosphate level decreases, calcium phosphate in the sorbent suspension dissolves and phosphate is released into the blood. Conversely, if the blood phosphate level increases, phosphate can be removed from the blood by precipitation of calcium phosphate in the sorbent suspension. The calcium-loaded cation exchanger moderates calcium concentration during these phosphate concentration changes. Accordingly, the sorbent suspension can be optimized to deliver more or less phosphate to a patient during treatment by adding, respectively, less or more calcium in the calcium-phosphate precipitation step in the preparation of the sorbent suspension. Because changes in blood concentrations of calcium and phosphate are not likely to be quantitatively the same during hyperthermia, 10% calcium chloride solution can also be kept available for infusion separately into blood returning to the patient, as needed.

Preferred sorbent suspensions including precipitated calcium phosphate are carefully prepared to assure that the calcium phosphate precipitate has maximal surface area for release or adsorption of calcium phosphate; forming the precipitate on the surface of the charcoal or other surface adsorptive agent achieves this goal. A preferred process for preparing a sorbent suspension includes adding sterile water for irrigation to a vessel (e.g. a sorbent bag as described above) which contains activated charcoal powder and flow-inducing agents. Calcium chloride and sodium chloride electrolyte solutions, and a disodium phosphate solution, are then added to the vessel. The mixture is then agitated, e.g. by shaking the sorbent bag, and the cation-exchange resin added (pre-loaded with sodium, calcium, magnesium, and potassium). The contents are agitated again, and then sodium bicarbonate powder is added, followed by further agitation. This process effectively prepares a sorbent suspension containing precipitated calcium phosphate, and which is essentially free from limestone.

In such a sorbent system, the surface adsorptive agent provides surface area on which substantial amounts of calcium phosphate can be supported, and thus in the overall sorbent suspension calcium phosphate will be present supported by the surface adsorptive agent as well as generally in the mixture.

In the present invention, the cation exchanger of the preferred sorbent suspension also has some buffering effect, to assist in maintaining normal blood pH.

An exemplary sorbent suspension contains: 140 grams powdered activated charcoal; 22.1 grams $NaHPO_4*7H_2O$ and 3.0 grams $CaCl*2H_2O$ (added together to the charcoal suspension); 200 grams Amberlite IRP-69 cation exchange resin loaded with blood equilibrium levels of Na, Ca, Mg and K ions; 13.0 grams NaCl; 15.1 grams $NaHCO_3$; and 1.5 grams of each a glycol derivative and PVP to enhance stability and flow properties of the sorbent suspension. This is an example only, and is not intended to be limiting.

During hyperthermia, there may be other toxins which evolve, due to diminished kidney or liver function. The surface adsorptive agent (e.g. charcoal) and cation exchangers in the sorbent suspension will remove many of these toxins, including: creatinine; aromatic amino acids; gamma-amino butyric acid; phenols; mercaptans; ammonium ion; nitric oxides; and various vasodilating hormones. Naturally, the sorbent suspension is not intended to remove proteins, intercellular messengers or cells, although to the degree that albumin-bound toxins can dissociate from albumin, these can also transfer across the membranes and be bound by the sorbents in the suspension.

In addition, during hyperthermia, additional calcium chloride may be infused to the patient (e.g. through a blood return line of the apparatus) as necessary to maintain normal blood calcium concentration. Also, plasma phosphate levels may be analyzed during hyperthermia and disodium phosphate added to the sorbent suspension whenever patient plasma phosphate levels fall below normal. This addition may be made using a solution of disodium phosphate and sodium bicarbonate, for example.

Most preferably, the sorbent suspension is maintained at moderate temperatures so that the blood tubing, dialyzer and sorbent suspension containers contact blood only at modestly elevated temperatures. Temperatures of 42° C. are suitable for these purposes, although higher temperatures, for example up to 48° C. or more, may also be used. The heat exchanger and the tubing returning blood to the patient will contact blood at temperatures of about 47–48° C. in preferred processes. These same components are used in open heart surgery to warm patients and safety of contact with blood at these temperatures has been thoroughly documented. Prior to hyperthermia treatment in accordance with the invention, patients are screened for underlying heart disease; underlying lung disease (including pulmonary Kaposi's Sarcoma if one or more lesions is greater than a certain size); pregnancy; a Karnofsky score of less than 60%; a non-correctable hematocrit of less than 30 ml.; hemoglobin less than 10%; active opportunistic infection; bleeding disorders; or Diabetes Mellitus. Any of the foregoing warrants careful consideration of the risks versus the benefits of hyperthermia treatment, since an important consideration in the practice of the present technique is whether the patient can tolerate it. The prehyperthermia evaluation requires a routine history and physical examination, routine laboratory studies, chest x-rays, urinalysis, electrocardiogram and pulmonary function studies. Special studies include P-24 antigen level assay; reverse transcriptase assay; human immunodeficiency virus cultures; lymphocyte quantitative analysis and thyroid profile.

Hyperthermia protocols can be conducted using conscious sedation, analgesics, or anesthetics (and intubation). The use of sedative amounts—as distinct from anesthetic amounts—of thiopental sodium can thus be used. An exemplary analgesic is commercially available as Sublimaze (fentanyl citrate, or N-(1-phenethyl-4-piperidyl) propionanilide citrate), a synthetic narcotic analgesic. An exemplary conscious sedation-inducing drug is Propofol, which is a sedative (or hypnotic agent) widely used in outpatient applications. The chemical formula for Propofol is 2,6-diisopropylphenol; the commercial name is Diprivan injection. These drugs are exemplary only, and the invention is not to be considered as limited to these illustrative medications. (However, Versed (midazolam hydrochloride, or 8-chloro-6-(2-fluorophenyl)-1-methyl-4H-imidazol[1,5-a][1,4] benzodiazepine hydrochloride), a short-acting benzodiazepine central nervous system depressant, should not be used, and other benzodiazepine derivatives are likewise contraindicated. Midazolam hydrochloride and benzodiazepine derivatives in general are biologically incompatible with hyperthermia: while Versed demonstrates typical pharmacologic activity (including reversibility) during the present procedure, the combination of the hyperthermia with the body biochemistry incident to hyperthermia causes disastrous central nervous system trauma (and possible death) six hours after the procedure is complete.) With the patient sedated, but not unresponsive, central nervous system activity can readily be monitored during hyperthermia treatment. When the sorbent-based hemodialysis is used, the sorbents clear approximately 50% of the sedative from the bloodstream. Therefore, administration of approximately twice the dosage of sedative will give the same sedative effect as when no dialysis is used.

Modification of the sorbent suspension may also be used to control other blood chemistries. For example, the sorbent suspension may be loaded with a sedative such as thiopental sodium to be in equilibrium with a level causing sedation. The patient blood level would then quickly rise to this level during hyperthermia treatments of the invention. Further sedation could be achieved by administering an injection of thiopental sodium to the blood; the pre-loaded sorbent suspension would then not remove significant amounts of the drug during treatment. Other agents for augmenting the hyperthermia treatment could also be loaded into the sorbent suspension and delivered during treatment, to maintain a reasonably constant blood concentration of the agents.

Because of the patient's natural depletion of carbohydrate and fat stores, these substances should be administered during and/or after treatment to assure that these precursors are adequately available to marginally competent metabolic pathways. Hemodialysis maintains levels of phosphate and calcium during treatment—which levels would otherwise fall as a result of the hyperthermia—especially when acid/bicarbonated water is used as the dialyzing solution. Maintenance of arterial oxygen tensions as high as possible during hyperthermia by use of 100% oxygen for ventilation should satisfy the need to maintain greater than normal blood and tissue oxygen tensions necessitated by hyperthermia-increased oxygen consumption.

While the invention has been described in detail in the foregoing passages, the same is to be considered illustrative and not restrictive in character, it being understood that only the preferred embodiments have been shown and described and that all changes and modifications that come within the spirit of the invention are desired to be protected.

REFERENCES

The following references, and all other publications cited herein, are hereby incorporated by reference as if each had been individually incorporated by reference and fully set forth.

1. Bull J M D. An update on the anticancer effects of a combination of chemotherapy and hyperthermia. Cancer Res 1984; 44:487.
2. Robins H I, Dennis W H. Role of whole body hyperthermia in the treatment of neoplastic disease: its current status and future prospects. Cancer Res 1984; 44:487.
3. Hornback N B. Historical aspects of hyperthermia in cancer therapy. Radiologic Clinics of North America 1989; 27:481–488.
4. Cavaliere R, Ciocatto E C, Giovanella B C, et al. Selective heat sensitivity of cancer cells: Biochemical and clinical studies. Cancer 1967; 20:1351.
5. Mondovi B, Strom R, Rotilio G, et al. The biochemical mechanisms of selective heat sensitivity of cancer cells. I: Studies on cellular respiration. Eur J Cancer 1969; 5:129.
6. Reinhold H S, van den Berg A P. Effects of hyperthermia on blood flow and metabolism. In: Field S B, Hand J W, ed. An introduction to the practical aspects of clinical hyperthermia. London; Taylor & Francis 1990; 77–107.
7. Kosa S, Maeta M. Extracorporeally induced total-body hyperthermia for disseminated cancer. Consensus on Hyperthermia for the 1990s, Clinical Practice in Cancer Treatment; 177–188.
8. Beral V et al. Kaposi's sarcoma among persons with AIDS: a sexually transmitted infection? Lancet 1990; 335:123–8.
9. Special data run by CDC from a series of Year-End Editions. U.S. Department of Health and Human Services, Public Health Service, Centers for Disease Control and Prevention, National Center for Infectious Diseases, Division of HIV/AIDS, Atlanta, Ga. Received March 1993.
10. DeMoss J L, Frazier T G, Crowley J C. Hyperthermia in the treatment of cancer. J Extra Corp Ther 1985; 17:37–43.
11. Logan W D, Alonso K. Case report: total body hyperthermia in the treatment of Kaposi's sarcoma in and HIV positive patient. Med Oncol and Tumor Pharmacother 1991; 8:45–47.
12. O'Malley S. Hyperthermia: perfusion's answer to AIDS? Perfusion Life, January 1991; 6–13.
13. Koga S, Maeta M. Extracorporeally induced total-body hyperthermia for disseminated cancer. In: Bicher H I, McLaren J R, Pigliucci G M, ed. Consensus on hyperthermia for the 1990s, Clinical practice in cancer treatment. New York; Plenum Press 1990; 177–188.
14. Shen R-N, Hornback N B, Shidnia H, Lu L, Broxmeyer H E, Brahmi Z. Effect of whole-body hyperthermia and cyclophosphamide on natural killer cell activity in murine erythroleukemia. Cancer Research 1988; 48:4561–4563.
15. Shen R-N, Lu L, Broxmeyer HE. New therapeutic strategies in the treatment of murine diseases induced by virus and solid tumors: biology and implications for the potential treatment of human leukemia, AIDS, and solid tumors. Critical Reviews in Oncology/Hematology 1990; 10:253–265.
16. McDougal J S, Martin L S, Curt S P, et al. Thermal inactivation of the acquired immunodeficiency syndrome virus human T. lymphotropic virus III/lymphoadenopaty associated virus, with special reference to antihemophilic factor. J Clin Invest 1985; 76:875.
17. Spire B, Sinoussi B F, Dormont D, Montaignet L, et al. Inactivation of lymph adenopathy-associated virus by heat-gamma rays, and ultraviolet light. Lancet 1985; 1:188.
18. Barklis E, Yatvin M. The life cycle of retroviruses: the influence of hyperthermia and membrane organization. Membrane Interactions of HIV 1992, 215–236.
19. Yatvin M B, Cramp W A. Role of cellular membranes in hperthermia: some observations and theories reviewed. Int J Hyperthermia 1993; 9:165–185.
20. Parks L C, Minaberry D P, Smith D P, Neely W A. Treatment of far advanced bronchogenic carcinoma by extracorporeally induced systemic hyperthermia. Thorac Cardiovasc Surg 1979; 78:881.
21. Larkin J M, Edwards W S, Smith D E, Clark P J. Systemic thermotherapy: description of a method and physiologic tolerance in clinical subjects. Cancer 1977; 40:3155–3159.
22. Parks L C, Smith G V. Systemic hyperthermia by extracorporeal induction: Techniques and results. In: Storm F, ed. Hyperthermia in Cancer Therapy, Boston, G K Hall Medical Publishers, 1983;407–446.
23. Bull J M, Lees D, Schuette W, Whang-Peng J, et al. Whole body hyperthermia: a phase-I trial of a potential adjuvant to chemotherapy. Ann Intern Med 1979; 90:317–323.
24. Parks L C, Minaberry D, Smith D P, et al. Treatment of far-advanced bronchogenic carcinoma by extracorporeally induced systemic hyperthermia. J Thorac Cardiovasc Surg 1979; 78:883–897.
25. Bull J M, Lees D E, Schuette W H, Smith R, Glatstein E, DeVita V T. Immunological and physiological responses to whole-body hyperthermia. Presented at the Third International Symposium: Cancer Therapy by Hyperthermia, Drugs, and Radiation held at Colorado State University, Ft. Collins, Colo., Jun. 22–26, 1980.
26. Robins H I, Hugander A, Cohen J D. Whole body hyperthermia in the treatment of neoplastic disease. Radiol Clin N Amer 1989; 27:603–610.
27. Yatvin M B, Stowell M H B, Steinhart C R. Shedding Light on the Use of Heat to Treat HIV Infections. Oncology 1993; 50:380–389.
28. Yatvin M B. An Approach to AIDS Therapy Using Hyperthermia and Membrane Modification. Medical Hypotheses 1988; 27:163–165.
29. Alonso K, Pontiggia P, Sabato A, Calvi G, Curto F C, de Bartolomei E, Nardi C, Cereda P. Systemic Hyperthermia in the Treatment of HIV Related Disseminated Malignancy, Presented at the 10th Annual Meeting, American Soc. Clin. Hyperthermic Oncology, October 1993, Memphis, Tenn.
30. U.S. Pat. No. 5,277,820.
31. U.S. Pat. No. 5,476,444.

What is claimed is:

1. An apparatus for use in whole body hyperthermia treatment of a patient, comprising:

a high-flow hyperthermia circuit equipped to circulate blood therethrough at a rate of at least 1500 ml/min, said high-flow hyperthermia circuit including a blood access line for drawing blood from a patient, a pump, a heat exchanger for heating the blood to a temperature of at least 40° C., and a blood return line for returning the blood to the patient after heating in the heat exchanger;

a low-flow dialysis circuit equipped to circulate blood therethrough at a rate of 200 to 800 ml/min, said low-flow dialysis circuit being coupled to the hyperthermia circuit and effective to divert from said hyperthermia circuit a portion of the blood circulating therein, said low-flow dialysis circuit including:

a blood inflow line having a first end connected to the hyperthermia circuit, for diverting blood into said dialysis circuit from said hyperthermia circuit;

a dialyzer having a blood side and a sorbent side separated by dialysis membranes, said membranes being compliantly formed;

means for applying alternating negative pressure and positive pressure on said sorbent side of said dialyzer;

a blood inlet to said blood side of said dialyzer, a second end of said blood inflow line being connected to said blood inlet; a blood outlet from said blood side of said dialyzer;

a blood outflow line having a first end connected to said blood outlet, and a second end connected to said hyperthermia circuit;

a sorbent circuit for circulating a sorbent suspension through said sorbent side of said dialyzer; and wherein said apparatus is configured such that during operation of said high-flow hyperthermia circuit and said low-flow dialysis circuit, said dialyzer membranes expand and compress in response to said alternating negative pressure and positive pressure on said sorbent side of said dialyzer, so as to circulate and agitate a sorbent suspension in said sorbent side whereby effective mixing of said sorbent suspension is maintained.

2. The apparatus of claim 1, which also includes:

a heat exchanger in the dialysis circuit, for heating heating the sorbent suspension.

3. The apparatus of claim 2, wherein the blood inflow line is connected to the high-flow hyperthermia circuit at a location downstream of the blood outflow line.

4. The apparatus of claim 3, wherein the blood inflow line and the outflow line are connected to the hyperthermia circuit on opposed sides of the pump.

5. The apparatus of claim 3, wherein the sorbent suspension includes precipitated calcium phosphate, water, and a particulate surface adsorptive agent.

6. The apparatus of claim 5, wherein said surface adsorptive agent is carbon.

7. The apparatus of claim 6, wherein said expansion and contraction of said membranes causes circulation of said blood in said low-flow dialysis circuit.

8. A process for preparing a sorbent suspension, comprising combining an aqueous solution having dissolved calcium ions with an aqueous solution having dissolved phosphate ions, wherein said combining is in the presence of a powdered surface adsorptive agent so as to form precipitated calcium phosphate both on the adsorptive agent and freely in the suspension, wherein said process comprises (a) combining water, activated charcoal powder and a flow-inducing agent;

(b) adding separate solutions containing, respectively, dissolved calcium chloride and dissolved disodium phosphate, to the product of step (a);

(c) agitating the product of step (b);

(d) adding a sodium, calcium, magnesium and potassium-loaded cation exchange resin to the product of step (c);

(e) agitating the product of step (d);

(f) adding sodium bicarbonate powder to the product of step (e); and (g) agitating the product of step (f).

* * * * *